United States Patent
Komatsu et al.

(10) Patent No.: US 8,865,952 B2
(45) Date of Patent: Oct. 21, 2014

(54) PROCESS FOR PRODUCING FLUORINE-CONTAINING ALKENE

(75) Inventors: Yuzo Komatsu, Settsu (JP); Daisuke Karube, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 15 days.

(21) Appl. No.: 13/575,403

(22) PCT Filed: Feb. 8, 2011

(86) PCT No.: PCT/JP2011/053061
§ 371 (c)(1),
(2), (4) Date: Jul. 26, 2012

(87) PCT Pub. No.: WO2011/099604
PCT Pub. Date: Aug. 18, 2011

(65) Prior Publication Data
US 2012/0302802 A1   Nov. 29, 2012

Related U.S. Application Data

(60) Provisional application No. 61/282,429, filed on Feb. 12, 2010.

(51) Int. Cl.
*C07C 17/25* (2006.01)
*C07C 19/08* (2006.01)
*C07C 21/18* (2006.01)

(52) U.S. Cl.
CPC ..................................... *C07C 17/25* (2013.01)
USPC .......................................... 570/156; 570/155

(58) Field of Classification Search
USPC .................................................. 570/156, 155
See application file for complete search history.

(56) References Cited

U.S. PATENT DOCUMENTS

| | | | | |
|---|---|---|---|---|
| 299,655 | A * | 6/1884 | Rausch et al. ................... | 299/78 |
| 6,359,183 | B1 * | 3/2002 | Christoph et al. ............ | 570/156 |
| 2007/0100175 | A1 * | 5/2007 | Miller et al. .................... | 570/178 |

FOREIGN PATENT DOCUMENTS

| | | | |
|---|---|---|---|
| EP | 0 223 906 | | 6/1987 |
| EP | 0 406 748 | | 1/1991 |
| EP | 406748 | A2 * | 1/1991 |
| WO | 2007/053178 | | 5/2007 |
| WO | 2007/079435 | | 7/2007 |
| WO | 2008/040969 | | 4/2008 |
| WO | WO 2008040969 | A2 * | 4/2008 |
| WO | 2008/054781 | | 5/2008 |
| WO | WO 2008054781 | A1 * | 5/2008 |
| WO | 2009/105512 | | 8/2009 |
| WO | WO 2009105512 | A1 * | 8/2009 |
| WO | WO 2009125200 | A2 * | 10/2009 |
| WO | WO 2009125201 | A2 * | 10/2009 |
| WO | 2009/138764 | | 11/2009 |
| WO | 2010/013795 | | 2/2010 |
| WO | WO 2010013795 | A1 * | 2/2010 |
| WO | WO 2010013796 | A1 * | 2/2010 |
| WO | 2010/123154 | | 10/2010 |

OTHER PUBLICATIONS

International Search Report issued Aug. 22, 2011 in International (PCT) Application No. PCT/JP2011/053061.
Written Opinion of the International Searching Authority issued Aug. 22, 2011 in International (PCT) Application No. PCT/JP2011/053061, of which the present application is the national stage.

* cited by examiner

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

The present invention provides a process for producing fluorine-containing alkene represented by Formula (2): $Rf1C(Rf2)=CH2$ wherein $Rf1$ and $Rf2$ are the same or different, and are F, H, $F(CF2)n-$ wherein n is an integer of 1 to 5, or $H(CF2)m-$ wherein m is an integer of 1 to 5, with the proviso that $Rf1$ and $Rf2$ are not simultaneously H, by heating fluorine-containing alkane represented by Formula (1): $Rf1CF(Rf2))CH3$ wherein $Rf1$ and $Rf2$ are as defined above, in a gas phase to perform a dehydrofluorination reaction, the dehydrofluorination reaction being carried out in the presence of 5 mol or more of anhydrous hydrogen fluoride per mol of the fluorine-containing alkane. The process of the present invention can significantly enhance the selectivity of fluorine-containing alkene without reducing conversion in the production of fluorine-containing alkene from fluorine-containing alkane, such as fluorine-containing propane.

12 Claims, No Drawings

PROCESS FOR PRODUCING FLUORINE-CONTAINING ALKENE

This application claims the benefit of U.S. provisional application No. 61/282,429, filed on Feb. 12, 2010, the contents of which are incorporated by reference.

TECHNICAL FIELD

The present invention relates to a process for producing fluorine-containing alkene.

BACKGROUND ART

A known process for producing fluorine-containing propene, such as 2,3,3,3-tetrafluoropropene (HFO-1234yf), comprises reacting chlorine-containing propane or chlorine-containing propene, which is used as a starting material, with anhydrous hydrogen fluoride in a gas phase in the presence of a catalyst, such as chrome oxide and fluorinated chrome oxide.

In this process, fluorine-containing propanes, such as 1,1,1,2,2-pentafluoropropane (HFC-245cb), are produced, in addition to the target fluorine-containing propene. Such fluorine-containing propanes can be converted to fluorine-containing propenes by dehydrofluorination, and are therefore useful as precursors of HFO-1234yf or other fluorine-containing propenes.

A known process for producing fluorine-containing propene from fluorine-containing propane, such as HFC-245cb, comprises, for example, subjecting HFC-245cb to dehydrofluorination, thereby producing HFO-1234yf (see PTL 1, listed below). In this process, HFO-1234yf is reportedly produced at a conversion of about 70 to 90% and with a selectivity of about 40 to 70%, by subjecting HFC-245cb, which is used as a starting material, to dehydrofluorination in the presence of activated carbon or activated carbon on which Ni, Pd, Pt, etc. are supported.

Additionally, there is a known process for producing HFO-1234yf by dehydrofluorination using fluorinated alumina or porous carbon as a catalyst (see PTL 2, listed below).

In these processes, however, the conversion of starting materials and the selectivity of fluorine-containing propene are not sufficient; particularly, further improvement in selectivity is required.

CITATION LIST

Patent Literature

PTL 1: WO 2007/079435
PTL 2: WO 2007/053178

SUMMARY OF INVENTION

Technical Problem

The present invention has been accomplished in view of the current status of the prior art described above. A primary object of the invention is to provide a novel process for producing fluorine-containing alkene from fluorine-containing alkane, such as fluorine-containing propane, the method being capable of reducing the production of by-products and enhancing the selectivity of fluorine-containing alkene, without reducing conversion.

Solution to Problem

The present inventors conducted extensive research to achieve the above object. Consequently, they found a surprising phenomenon that, when the reaction is carried out in a gas phase in the presence of a certain concentration or higher of anhydrous hydrogen fluoride in the production of fluorine-containing alkene from fluorine-containing alkane, the selectivity of fluorine-containing alkene is significantly enhanced, even though the reaction proceeds by dehydrofluorination. The present invention has been accomplished upon further studies based on these novel findings.

More specifically, the present invention provides the following process for producing a fluorine-containing alkene.

Item 1. A process for producing fluorine-containing alkene represented by Formula (2):

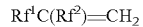

$Rf^1C(Rf^2)=CH_2$ wherein $Rf^1$ and $Rf^2$ are the same or different, and are F, H, $F(CF_2)_{n-}$ wherein n is an integer of 1 to 5, or $H(CF_2)_{m-}$ wherein m is an integer of 1 to 5, with the proviso that $Rf^1$ and $Rf^2$ are not simultaneously H, the process comprising heating fluorine-containing alkane represented by Formula (1):

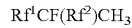

$Rf^1CF(Rf^2)CH_3$ wherein $Rf^1$ and $Rf^2$ are as defined above, in a gas phase in the presence of 5 mol or more of anhydrous hydrogen fluoride per mol of the fluorine-containing alkane to perform a dehydrofluorination reaction.

Item 2. The process according to Item 1, wherein the fluorine-containing alkane used as a starting material is represented by Formula (1-1):

$Rf^1CF(Rf^3)CH_3$ wherein $Rf^1$ is F, H, $F(CF_2)_{n-}$ wherein n is an integer of 1 to 3, or $H(CF_2)_{m-}$ wherein m is an integer of 1 to 3, and $Rf^3$ is F or H, with the proviso that $Rf^1$ and $Rf^3$ are not simultaneously H:

Item 3. The process according to Item 1 or 2, wherein the reaction is carried out in the presence of a catalyst.

Item 4. The process according to Item 3, wherein the reaction is carried out in the presence of a chromium atom-containing catalyst.

Item 5. The process according to any one of Items 1 to 4, wherein the reaction is carried out in the presence of 10 to 200 mol of anhydrous hydrogen fluoride per mol of the fluorine-containing alkane.

The process for producing a fluorine-containing alkene of the present invention is described in detail below.

Fluorine-Containing Alkane

In the present invention, fluorine-containing alkane represented by Formula (1): $Rf^1CF(Rf^2)CH_3$ is used as a starting material. In Formula (1), $Rf^1$ and $Rf^2$ are the same or different, and are F, H, $F(CF_2)_{n-}$ (n is an integer of 1 to 5), or $H(CF_2)_{m-}$ (m is an integer of 1 to 5), with the proviso that $Rf^1$ and $Rf^2$ are not simultaneously H.

In Formula (1), the amount of decomposition by-products tends to be increased as the total carbon number of $Rf^1$ and $Rf^2$ increases. For this reason, preferred examples of the fluorine-containing alkane represented by Formula (1) particularly include fluorine-containing alkane represented by Formula (1-1): $Rf^1CF(Rf^3)CH_3$, wherein $Rf^1$ is F, H, $F(CF_2)_{n-}$ (n is an integer of 1 to 3), or $H(CF_2)_{m-}$ (m is an integer of 1 to 3), and $Rf^1$ is F or H, with the proviso that $Rf^1$ and $Rf^3$ are not simultaneously H; and the like.

Specific examples of the fluorine-containing alkane include 1,1,1,2,2-pentafluoropropane (HFC-245cb), 1,1,2,2-tetrafluoropropane (HFC-254cb), 1,1,1,2-tetrafluoropropane (HFC-254eb), 1,1,1-trifluoroethane (HFC-143a), 1,1-difluoroethane (HFC-152a), 1,1,1,2,2,3,3-heptafluorobutane (HFC-347mccs), and the like.

These examples of the fluorine-containing alkane represented Formula (1) are easily available known compounds.

Process for Producing Fluorine-Containing Alkene

In the process for producing fluorine-containing alkene of the present invention, fluorine-containing alkane, as described above, is used as a starting material, and is heated in a gas phase to perform a dehydrofluorination reaction, thereby obtaining fluorine-containing alkene.

In the present invention, when fluorine-containing alkene is produced from fluorine-containing alkane by the above process, a certain amount or more of anhydrous hydrogen fluoride is required to exist in the reaction system. Thereby, the selectivity of fluorine-containing alkene can be greatly enhanced while hardly reducing the conversion of the starting material, even though the reaction proceeds by dehydrofluorination.

In order to achieve the effect of improving the selectivity, the amount of anhydrous hydrogen fluoride in the reaction system is required to be about 5 mol or more, preferably about 10 mol or more, and more preferably about 50 mol or more, per mol of fluorine-containing alkane, which is used as a starting material. An amount of anhydrous hydrogen fluoride below this range is not preferred because the effect of improving selectivity is not sufficiently exhibited.

The upper limit of the amount of hydrogen fluoride is not particularly limited. An overly large amount of hydrogen fluoride has little influence on selectivity and conversion; however, productivity is reduced because the amount of hydrogen fluoride to be separated increases during purification. Accordingly, it is generally preferable that the amount of anhydrous hydrogen fluoride is about 200 mol or less, per mol of the fluorine-containing alkane.

The process of the present invention can be carried out in the presence or absence of a catalyst. Particularly, when the dehydrofluorination reaction is carried out in the presence of a catalyst, the reaction temperature can be reduced, while the selectivity can be further enhanced.

As a catalyst, known catalysts usable in the dehydrohalogenation reaction can be used. Examples thereof include halides and oxides of transition metals, Group 14 and 15 elements, etc. Metal elements in such catalysts have high affinity for a fluorine atom to be removed, and are therefore considered to have an effect of promoting the dehydrofluorination reaction. Specific examples of transition metals include Ti, V, Cr, Mn, Fe, Co, Ni, Cu, Zn, Zr, Nb, Ta, W, etc. Specific examples of Group 14 elements include Sn, Pb, etc. Specific examples of Group 15 elements include Sb, Bi, etc. Examples of halides of these elements include fluoride, chloride, etc. Among these, examples of preferable catalysts include $SbCl_5$, $SbCl_3$, $SbF_5$, $TaCl_5$, $SnCl_4$, $NbCl_5$, $FeCl_3$, $CrCl_3$, $CrF_3$, $TiCl_4$, $MoCl_5$, $Cr_2O_3$, $CrO_2$, $CrO_3$, $CoCl_2$, $NiCl_2$, etc. These catalysts can be used singly or in combination of two or more. Alternatively, they can be supported on a carrier. The carrier to be used is not particularly limited, and examples thereof include porous alumina silicate represented by zeolite, aluminum oxide, silicon oxide, activated carbon, titanium oxide, zirconia oxide, zinc oxide, aluminum fluoride, and the like. These can be used singly or in combination thereof, or a structural composite form thereof. Specific examples of catalysts supported on a carrier include $Cr_2O_3/Al_2O_3$, $Cr_2O_3/AlF_3$, $Cr_2O_3/C$, $CoCl_2/Cr_2O_3/Al_2O_3$, $NiCl_2/Cr_2O_3/Al_2O_3$, $CoCl_2/AlF_3$, $NiCl_2/AlF_3$, etc.

In the present invention, it is preferable to use a chromium-atom containing catalyst, and it is particularly preferable to use at least one catalyst selected from the group consisting of chromium oxide and fluorinated chromium oxide. Examples of such chromium oxide and fluorinated chromium oxide include crystalline chromium oxide, amorphous chromium oxide, and the like.

The composition of chromium oxide is not particularly limited. For example, it is preferable to use chromium oxide represented by the composition formula $CrO_m$, wherein $1.5<m<3$, more preferably $2<m<2.75$, and even more preferably $2<m<2.3$. Any chromium oxide catalysts in the form of powder, pellets, etc. can be used, as long as they are suitable for the reaction. Particularly, pellet-type catalysts are preferred. The above chromium oxide catalyst can be produced, for example, by the process disclosed in Japanese Unexamined Patent Publication No. 5-146680.

The fluorinated chromium oxide can be produced by the process disclosed in Japanese Unexamined Patent Publication No. 5-146680. For example, it can be obtained by fluorinating the chromium oxide obtained by the above process with hydrogen fluoride (HF treatment). The temperature of fluorination may be, for example, about 100 to 460° C.

Although the surface area of the catalyst is decreased after fluorination treatment, the activity of the catalyst is generally higher with a larger specific surface area. The specific surface area after fluorination treatment is preferably about 25 to 130 $m^2/g$, and more preferably about 40 to 100 $m^2/g$, although not limited thereto. In the present specification, the specific surface area is measured by the BET method The fluorination reaction of chromium oxide can alternatively be carried out by supplying anhydrous hydrogen fluoride to a reactor filled with chromium oxide, prior to the dehydrofluorination reaction of fluorine-containing alkane. After chromium oxide is fluorinated in this manner, the starting material is supplied to the reactor, thereby efficiently promoting the production reaction of the desired product.

The degree of fluorination of the catalyst is not particularly limited; for example, the fluorine content is preferably about 5 to 30 wt %.

Further, the chromium-based catalyst disclosed in Japanese Unexamined Patent Publication No. 11-171806 can also be used as a chromium oxide catalyst or a fluorinated chromium oxide catalyst. The chromium-based catalyst is in an amorphous state, and comprises, as a main component, a chromium compound containing at least one metal element selected from the group consisting of indium, gallium, cobalt, nickel, zinc, and aluminum. The chromium in the chromium compound has an average valence number of not less than +3.5 and not more than +5.0.

Because the process of the present invention is carried out in the presence of hydrogen fluoride, the fluorination of the catalyst presumably proceeds during the reaction, even when the fluorination treatment is not previously carried out.

The method of using the catalyst is not particularly limited as long as the starting material gas is sufficiently in contact with the catalyst. For example, the catalyst can be fixed in a reactor, or dispersed in a fluidized bed.

In the process of the present invention for producing fluorine-containing alkene, the reaction process is not particularly limited as long as fluorine-containing alkane, which is used as a starting material, can be sufficiently heated in a gas phase.

In a specific example of an embodiment, a catalyst, when used, is charged into a tubular flow-type reactor, and fluorine-containing alkane and hydrogen fluoride, which are used as starting materials, are introduced into the reactor. The reactor is preferably formed of a material resistant to the corrosive action of hydrogen fluoride, such as Hastelloy, Inconel, Monel, or the like.

The above starting materials can be directly supplied into the reactor; or nitrogen, helium, argon and other gases that are inert to the starting materials and catalyst can be used in combination with the starting materials. The concentration of inert gas can be, for example, about 0 to 80 mol % based on the total amount of the gas components introduced into the reactor; that is, the amounts of fluorine-containing alkane and anhydrous hydrogen fluoride (starting materials) in addition to inert gas, and optionally the amount of oxygen gas, when added.

When a catalyst is used, the above starting materials can be supplied into the reactor together with oxygen to maintain catalytic activity for a long time. In this case, the amount of oxygen added can be, for example, about 0.1 to 50 mol % based on the total amount of the gas components including fluorine-containing alkane and anhydrous hydrogen fluoride (starting materials) in addition to oxygen, and optionally the amount of inert gas, when used. A larger amount of oxygen is not preferred because oxidation reaction and other side reactions occur, and selectivity decreases.

The reaction temperature, pressure, reaction time, and other conditions of the dehydrofluorination reaction in the present invention are not particularly limited. Optimal values may be determined in consideration of production efficiency, the selectivity of HFO-1234yf, the life of a catalyst, when used, etc.

Generally, the reaction temperature is preferably about 200 to 550° C., and more preferably about 300 to 450° C. At an overly low reaction temperature, the conversion of fluorine-containing alkane tends to decrease. Conversely, an overly high reaction temperature easily results in the production of C1 and C2 compounds by the decomposition of the starting materials, and the production of $Rf^1C(Rf^2)=CHF$ and other isomers as by-products. Thus, a temperature range outside the above-described range is not preferred.

Because the selectivity of fluorine-containing alkene tends to decrease at a higher reaction temperature, it is preferable to increase the proportion of hydrogen fluoride to fluorine-containing alkane to maintain high selectivity when the reaction is conducted at a higher temperature. For example, when the reaction temperature is 380° C. or more, it is preferable to use about 30 mol or more of anhydrous hydrogen fluoride per mol of fluorine-containing alkane.

The pressure during the reaction is not particularly limited, and the reaction can be carried out under reduced pressure, normal pressure, or increased pressure. Generally, the reaction may be carried out under about atmospheric pressure (0.1 MPa); however, the reaction can also smoothly proceed under a reduced pressure of less than 0.1 MPa. The reaction can also be carried out under increased pressure that does not liquefy the starting materials.

The reaction time is not limited. For example, when a catalyst is used, the contact time determined by the ratio $W/F_0$ of the amount W (g) of catalyst to the total flow rate $F_0$ of gas components flowed through the reaction system (flow rate at 0° C. and 0.1 MPa: cc/sec) is preferably about 0.1 to 90 g·sec/cc, and more preferably about 1 to 50 g·sec/cc. When no catalyst is used, the contact time determined by the ratio $V/F_0$ of the volume of space V (cc) to the total flow rate $F_0$ of gas components flowed through the reaction system (flow rate at 0° C. and 0.1 MPa: cc/sec) is preferably about 0.1 to 50 sec, and more preferably about 1 to 30 sec. The total flow rate of gas components herein used is the total flow rate of fluorine-containing alkane and anhydrous hydrogen fluoride, and optionally inert gas, oxygen, etc., when used.

According to the above process, fluorine-containing alkene represented by Formula (2): $Rf^1C(Rf^2)=CH_2$, wherein $Rf^1$ and $Rf^2$ are defined above, can be obtained with high selectivity by the dehydrofluorination reaction of fluorine-containing alkane represented by Formula (1): $Rf^1CF(Rf^2)CH_3$, which is used as a starting material. For example, when 1,1,1,2,2-pentafluoropropane (HFC-245cb) is used as a starting material, 2,3,3,3-tetrafluoropropene (HFO-1234yf) can be obtained with high selectivity.

The obtained product can be separated and collected by a generally used method, such as distillation. Further, unreacted starting materials can be recycled by being returned to the reactor after separation and purification. Thus, high productivity can be maintained by recycling unreacted starting materials.

Advantageous Effects of Invention

The production process of the present invention can greatly enhance the selectivity of fluorine-containing alkene in the production of fluorine-containing alkene from fluorine-containing alkane, such as fluorine-containing propane, without reducing conversion, compared with a conventional process.

Additionally, the process of the present invention can make beneficial use of fluorine-containing alkane that is produced as a by-product in a conventional process for producing fluorine-containing alkene, and efficiently convert it to fluorine-containing alkene.

Therefore, the process of the invention is industrially highly useful to produce fluorine-containing alkene.

DESCRIPTION OF EMBODIMENTS

The present invention is described in more detail below with reference to Examples.

Example 1

A catalyst (9.35 g; fluorine content: about 15.0 wt. %) obtained by fluorinating chrome oxide represented by the composition formula: $CrO_2$ was placed in a tubular Hastelloy reactor equipped with a back-pressure valve at its outlet, and having an inner diameter of 15 mm and a length of 1 m. The tubular reactor was maintained at atmospheric pressure (0.1 MPa) at 365° C. Anhydrous hydrogen fluoride (HF) gas and oxygen gas were supplied to the reactor at 28 cc/min and 0.11 cc/min (the flow rate at 0° C. and 0.1 MPa; the same applies hereinafter), respectively, for one hour. Thereafter, $CF_3CF_2CH_3$ (HFC-245cb) was supplied at 0.25 cc/min. The molar ratio of HF to HFC-245cb was 110 at this time. The outlet gas from the reactor after 6 hours was analyzed by gas chromatography. Table 1 shows the analysis results.

The chemical formula of each compound is as follows.

$CF_3CF_2CH_3$ (HFC-245cb)

$CF_3CF=CH_2$ (HFO-1234yf)

$CF_3CH=CHF$ (HFO-1234ze)

$CF_3CH_3$ (HFC-143a)

$CF_3CH_2CHF_2$ (HFC-245fa)

Example 2

The reaction was carried out under the same conditions as in Example 1, except that the flow rates of anhydrous hydrogen fluoride (HF) gas, oxygen gas, and HFC-245cb were changed to 221 cc/min, 0.44 cc/min, and 2.22 cc/min (the flow rate at 0° C. and 0.1 MPa), respectively. The molar ratio of HF to HFC-245cb was 100 at this time. Table 1 shows the analysis results of the outlet gas.

Example 3

The reaction was carried out under the same conditions as in Example 1, except that the reaction temperature was changed to 345° C. Table 1 shows the analysis results of the outlet gas.

Example 4

The reaction was carried out under the same conditions as in Example 1, except that the temperature was changed to 385° C. Table 1 shows the analysis results of the outlet gas.

Example 5

The reaction was carried out under the same conditions as in Example 1, except that the flow rates of anhydrous hydrogen fluoride (HF) gas, oxygen gas, and HFC-245cb were changed to 27 cc/min, 0.11 cc/min, and 0.55 cc/min (the flow rate at 0° C. and 0.1 MPa); respectively. The molar ratio of HF to HFC-245cb was 49 at this time. Table 2 shows the analysis results of the outlet gas.

Comparative Example 1

The reaction was carried out under the same conditions as in Example 1, except that anhydrous hydrogen fluoride (HF) gas was not supplied, and the flow rates of oxygen gas and HFC-245cb were changed to 5.0 cc/min and 25 cc/min (the flow rate at 0° C. and 0.1 MPa), respectively. The molar ratio of HF to HFC-245cb was 0 at this time. Table 2 shows the analysis results of the outlet gas.

Example 6

The reaction was carried out under the same conditions as in Example 1, except that the flow rates of anhydrous hydrogen fluoride (HF) gas, oxygen gas, and HFC-245cb were changed to 25 cc/min, 0.50 cc/min, and 2.5 cc/min (the flow rate at 0° C. and 0.1 MPa), respectively. The molar ratio of HF to HFC-245cb was 10 at this time. Table 2 shows the analysis results of the outlet gas.

TABLE 1

|  | Ex. 1 | Ex. 2 | Ex. 3 | Ex. 4 |
|---|---|---|---|---|
| Reaction temp. (° C.) | 365 | 365 | 345 | 385 |
| $W/F_0$ (g sec/cc) | 20 | 2.5 | 20 | 20 |
| HF/HFC245cb | 110 | 100 | 110 | 110 |
| HFC-245cb conversion (GC %) | 82 | 78 | 71 | 90 |
| HFO-1234yf selectivity (GC %) | 90 | 98 | 97 | 81 |
| HFO-1234ze selectivity (GC %) | 4.4 | 0.9 | 1.8 | 14 |
| HFC-143a selectivity (GC %) | 3.0 | 0.2 | 0.2 | 2.5 |
| HFC-245fa selectivity (GC %) | 0.7 | 0.1 | 0.5 | 1.4 |

TABLE 2

|  | Ex. 5 | Ex. 6 | Comp. Ex. 1 |
|---|---|---|---|
| Reaction temp. (° C.) | 365 | 365 | 365 |
| $W/F_0$ (g sec/cc) | 20 | 20 | 20 |
| HF/HFC245cb (GC %) | 49 | 10 | 0 |
| HFC-245cb conversion (GC %) | 82 | 80 | 74 |
| HFO-1234yf selectivity (GC %) | 88 | 84 | 79 |
| HFO-1234ze selectivity (GC %) | 5.9 | 6.8 | 6.9 |
| HFC-143a selectivity (GC %) | 3.1 | 1.1 | 2.8 |
| HFC-245fa selectivity (GC %) | 0.9 | 1.5 | 1.2 |

The invention claimed is:

1. A process for producing a compound of formula (2):

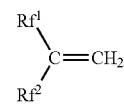

(2)

wherein $Rf^1$ and $Rf^2$ each individually are H, F or $X(CF_2)_n$- wherein n is an integer of 1-5 and X is F or H, with the proviso that $Rf^1$ and $Rf^2$ are not simultaneously H, comprising heating and dehydrofluorinating a compound of formula (1) wherein $Rf^1$ and $Rf^2$ are as defined above:

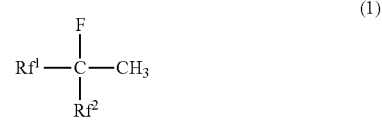

(1)

in a gas phase in the presence of >50 mol anhydrous HF per mol of compound (1).

2. The process of claim 1, wherein $Rf^1$ is H, F or $X(CF_2)_n$- wherein n is an integer of 1-3 and X is F or H, and $Rf^2$ is H or F.

3. The process of claim 1, wherein the reaction is carried out in the presence of a catalyst.

4. The process of claim 3, wherein the catalyst is a chromium atom-containing catalyst.

5. The process of claim 1, wherein the reaction is carried out in the presence of greater than 50 and less or equal to 200 mol of anhydrous HF per mol of compound (1).

6. The process of claim 2, wherein the reaction is carried out in the presence of a catalyst.

7. The process of claim 6, wherein the catalyst is a chromium atom-containing catalyst.

8. The process of claim 2, wherein the reaction is carried out in the presence of greater than 50 and less or equal to 200 mol of anhydrous HF per mol of compound (1).

9. The process of claim 3, wherein the reaction is carried out in the presence of greater than 50 and less or equal to 200 mol of anhydrous HF per mol of compound (1).

10. The process of claim 4, wherein the reaction is carried out in the presence of greater than 50 and less or equal to 200 mol of anhydrous HF per mol of compound (1).

11. The process of claim 6, wherein the reaction is carried out in the presence of greater than 50 and less or equal to 200 mol of anhydrous HF per mol of compound (1).

12. The process of claim 7, wherein the reaction is carried out in the presence of greater than 50 and less or equal to 200 mol of anhydrous HF per mol of compound (1).

* * * * *